(12) United States Patent
Sheldon

(10) Patent No.: US 8,246,166 B2
(45) Date of Patent: *Aug. 21, 2012

(54) EYEWEAR WITH REFLECTIVE HEAD STRAP

(76) Inventor: Brent Sheldon, Montreal (CA)

( * ) Notice: Subject to any disclaimer, the term of this patent is extended or adjusted under 35 U.S.C. 154(b) by 371 days.

This patent is subject to a terminal disclaimer.

(21) Appl. No.: 12/634,170

(22) Filed: Dec. 9, 2009

(65) Prior Publication Data

US 2010/0231852 A1    Sep. 16, 2010

Related U.S. Application Data

(63) Continuation-in-part of application No. 12/404,607, filed on Mar. 16, 2009, now Pat. No. 7,828,427.

(51) Int. Cl.
*G02C 3/00* (2006.01)

(52) U.S. Cl. ............ 351/156; 351/51; 351/52; 351/157

(58) Field of Classification Search .................. 351/156, 351/157, 51, 52, 121, 41, 158
See application file for complete search history.

(56) References Cited

U.S. PATENT DOCUMENTS

| | | |
|---|---|---|
| 1,555,388 A | 9/1925 | Schumacher |
| D151,698 S | 11/1948 | Levoy |
| D152,487 S | 1/1949 | Mangold |
| D172,671 S | 7/1954 | Kono |
| D178,307 S | 7/1956 | Margules |
| 2,766,541 A | 10/1956 | Quinones et al. |
| D205,097 S | 6/1966 | Mitchell |
| 4,266,849 A | 5/1981 | Warner |
| 4,715,702 A | 12/1987 | Dillon |
| 4,934,792 A | 6/1990 | Tovi |
| 5,892,600 A | 4/1999 | Kuo |
| 6,020,983 A | 2/2000 | Neu et al. |
| 6,641,262 B1 | 11/2003 | Cheng |
| 6,948,808 B1 | 9/2005 | Callahan |
| 7,163,290 B2 | 1/2007 | Paolino |
| 7,261,409 B1 | 8/2007 | Taber |
| 7,364,288 B2 | 4/2008 | Huang |
| 7,828,427 B2 * | 11/2010 | Sheldon ........................ 351/52 |
| 7,942,520 B2 * | 5/2011 | Sheldon ........................ 351/52 |
| 7,942,521 B2 * | 5/2011 | Sheldon ........................ 351/52 |

FOREIGN PATENT DOCUMENTS

| | | |
|---|---|---|
| CA | 2377390 | 10/2001 |
| CA | 2504575 | 10/2005 |
| GB | 1223173 | 2/1971 |

OTHER PUBLICATIONS

Tougaw, D. et al.; "Visualizing the Future of Virtual Reality"; Computing in Science & Engineering; vol. 5, No. 4, pp. 8-11, Jul./Aug. 2003.

(Continued)

*Primary Examiner* — Hung Dang

(74) *Attorney, Agent, or Firm* — Norton Rose Canada LLP

(57) ABSTRACT

Eyewear includes at least one lens, a frame having a main front section for supporting the lens attached to the main front section. The eyewear further includes a head strap attached to the frame and at least one retroreflective element attached to the head strap to be visible by others in low-light conditions.

16 Claims, 4 Drawing Sheets

OTHER PUBLICATIONS

International Search Report dated Jun. 22, 2010, issued by the Canadian Intellectual Property Office as the PCT Searching Authority, on Applicant's related PCT International Patent Application No. PCT/CA2010/000356.

International Search Report dated Jun. 7, 2010, issued by the Canadian Intellectual Property Office as the PCT Searching Authority, on Applicant's related PCT International Patent Application No. PCT/CA2010/000357.

* cited by examiner

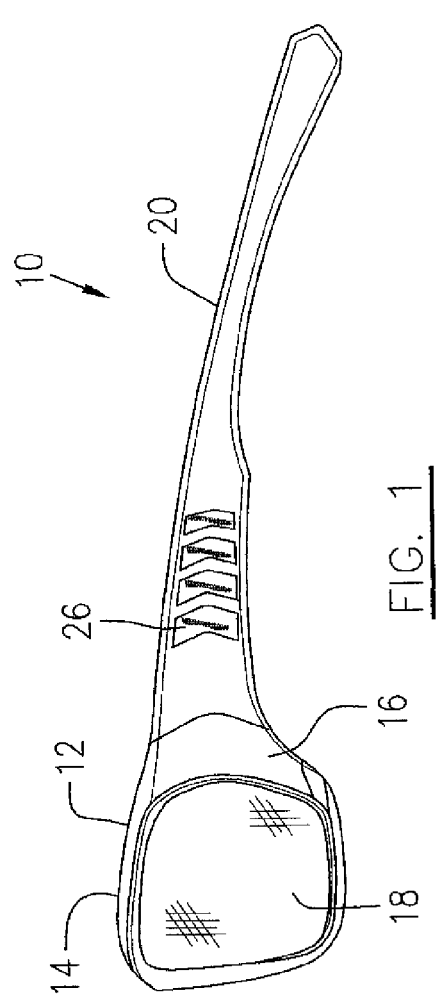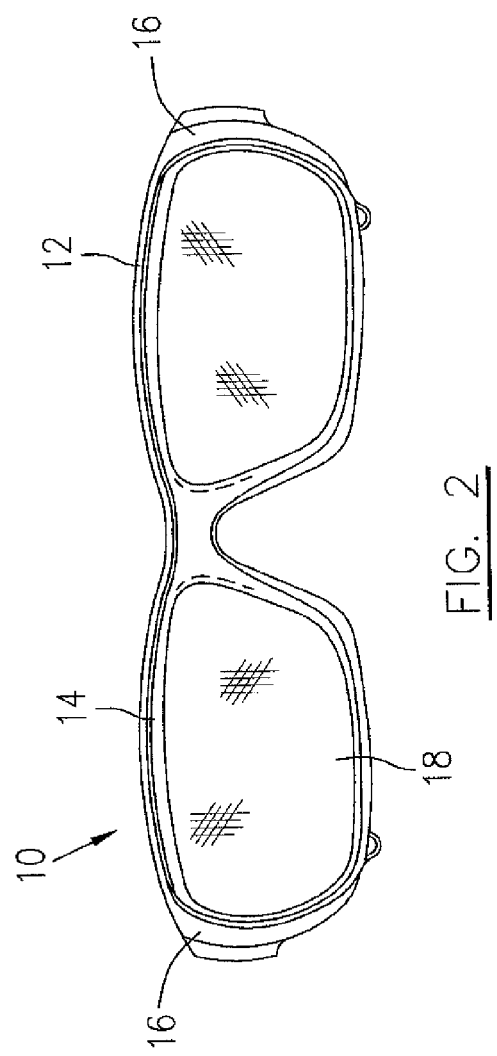

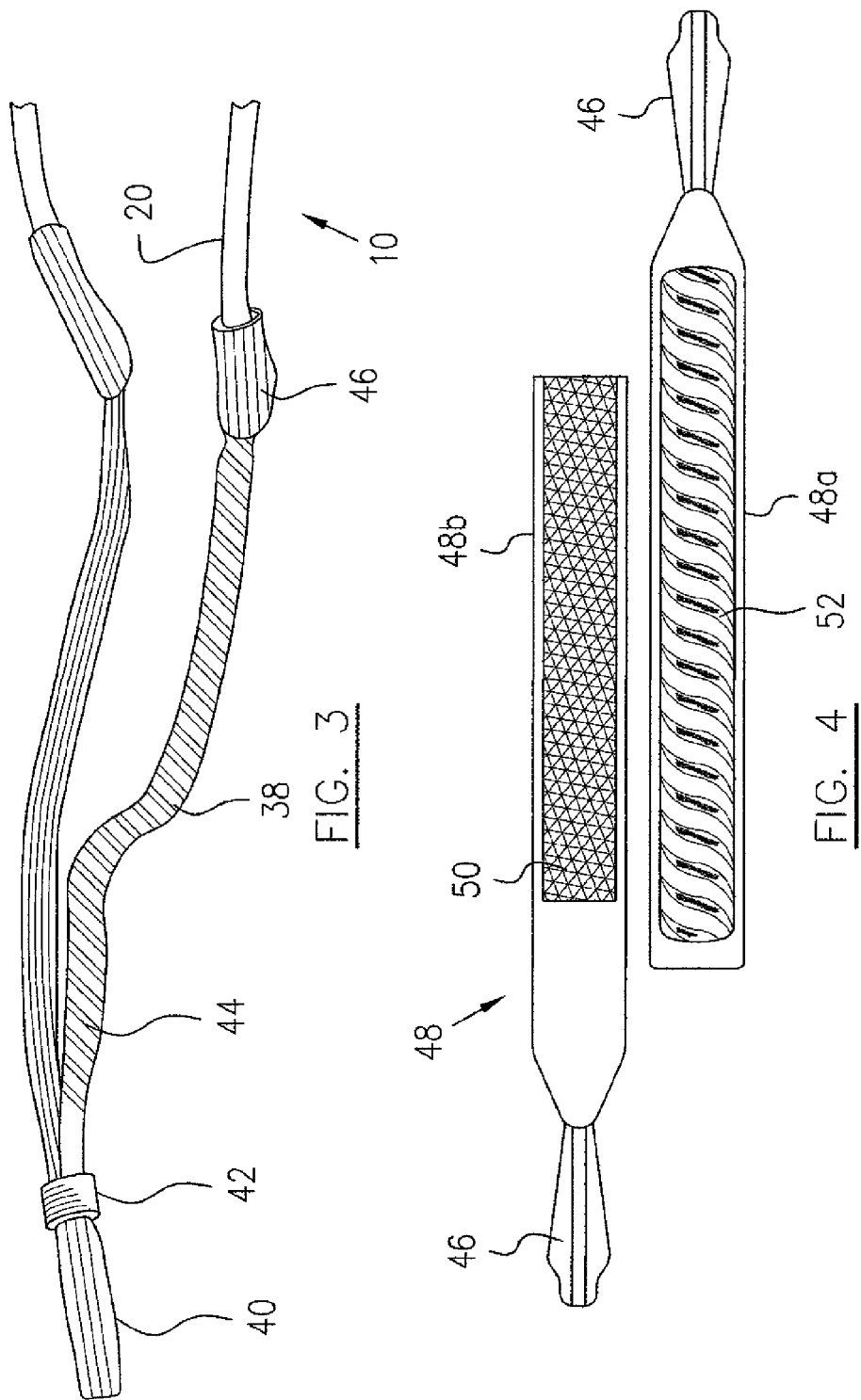

EYEWEAR WITH REFLECTIVE HEAD STRAP

CROSS-REFERENCE TO RELATED APPLICATIONS

This application is a Continuation-In-Part of Applicant's application Ser. No. 12/404,607, filed on Mar. 16, 2009, now U.S. Pat. No. 7,828,427.

TECHNICAL FIELD

The present invention relates to an improvement on a structure of glasses, and more particularly to a structure of glasses having a frame with attached retroreflective elements.

BACKGROUND OF THE INVENTION

Safety glasses are used to protect users' eyes from injuries, for example when participating in sports or while working. In some cases it is desirable to have safety glasses which are luminous or capable of reflecting light. However, such reflective safety glasses are currently not popular in the marketplace. The light-reflective feature of currently available safety glasses is not very effective due to the limited outer surface of glasses frames and the limited light reflecting capabilities of materials currently used with eyewear. It is also desirable to avoid interference with the user's vision, which may be caused by the reflection of the reflective elements of safety glasses into the user's eyes.

Accordingly, there is a need for an improved structure of reflective glasses.

SUMMARY OF THE INVENTION

In accordance with one aspect of the present invention, there is provided eyewear comprising: at least one lens; a frame having a main front section for supporting the at least one lens attached to the main front section; a head strap attached to the frame; and at least one retroreflective element attached to the head strap, the retroreflective element reflecting light rays of any incidence angles along a vector parallel to but in opposite direction from a light ray source.

Optionally, the head strap may comprise a flexible strap section extending between a pair of connectors. Also optionally, the retroreflective element may be attached to the flexible strap section and/or the connectors, respectively.

Other aspects or features of the present invention will be better understood with reference to the preferred embodiments described hereinafter.

BRIEF DESCRIPTION OF THE DRAWINGS

Reference is now made to the accompanying drawings, showing by way of illustration the preferred embodiments thereof, in which:

FIG. 1 is a side elevational view of reflective safety glasses according to one embodiment, having openings in the arms to expose the retroreflective elements attached thereto, with a head strap detached (not shown);

FIG. 2 is a front elevational view of the reflective safety glasses of FIG. 1;

FIG. 3 is a perspective view of a head strap attached to the glasses of FIG. 1 according to one embodiment;

FIG. 4 is an exploded side elevational view of a head strap according to another embodiment, showing separated right and left sections of the head strap;

It will be noted that throughout the appended drawings, like features are identified by like reference numerals.

DETAILED DESCRIPTION OF THE PREFERRED EMBODIMENTS

Figure 5:
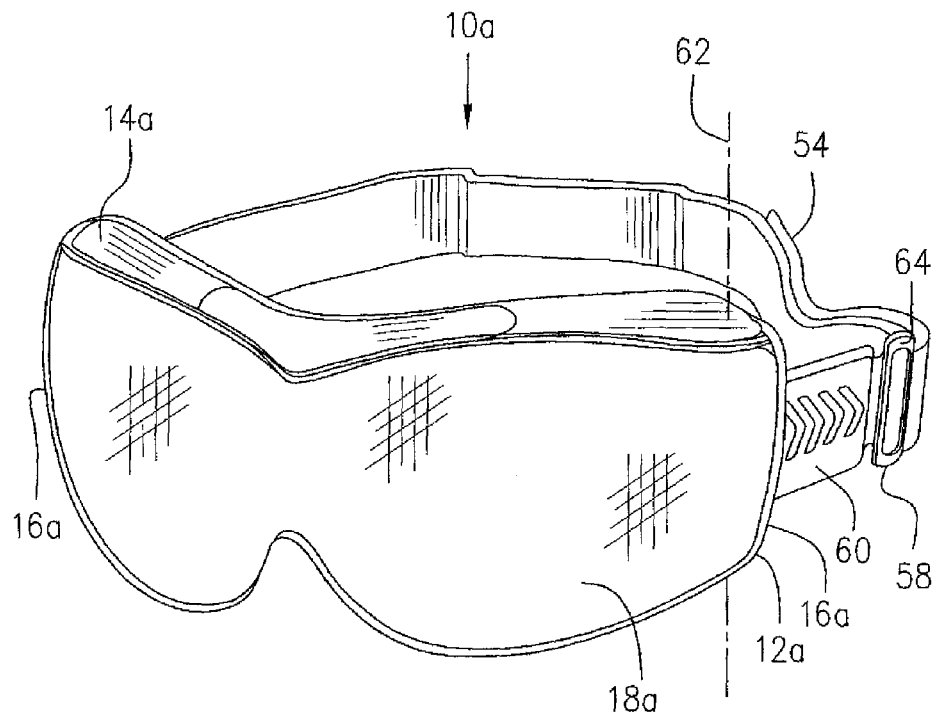
FIG. 5 is a perspective view of goggles according to another embodiment showing a retroreflective element attached to a connector of a head strap of the goggle.
Figure 6:
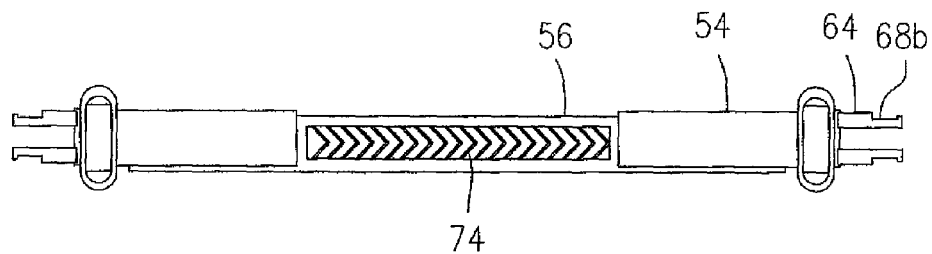
FIG. 6 is a side elevational view of the head strap of FIG. 5 showing a retroreflective element attached to a flexible strap section of the head strap.

Referring to FIGS. 1 through 3, a structure of reflective safety glasses 10 according to one embodiment generally includes a frame 12 which for example may be made of a plastic material in a molding process, having a main front section 14 with opposed side ends 16 for supporting one or two lenses 18. The frame 12 further includes a pair of side sections (not numbered) extending rearwardly from the respective opposed side ends 16 of the main front section 14. The rearwardly extending side sections of the frame 12 according to this embodiment, are a pair of arms 20 pivotally joined to the respective opposed side ends 16 of the main front section 14 in a conventional manner.

A head band or head strap 38 (referred to as a head strap hereinafter) which may be elastically extendable or flexible but not elastically extendable, is attached to the respective arms 20, for example, at the free ends of the arms 20. In this embodiment, a selected length of a section 40 of the head strap may be restrained by a restraining ring 42 in a folded condition and the effective length of the head strap 38 may be adjusted by moving the position of the restraining ring 42 around the folded section 40. The effective length of the head strap 38 may be adjusted short to be held around the user's head when the glasses 10 is in use, or adjusted long to be hung around the user's neck when the glasses 10 is not in use.

One or more retroreflective elements 26 may be attached to each of the side sections which are the respective arms 20 in this embodiment, such that the attached retroreflective elements are visible by others in low-light conditions. The details of this and other embodiments were described in the parent U.S. application Ser. No. 12/404,607 filed on Mar. 16, 2009, which is incorporated herein by reference.

Retroreflective materials, such as 3M™ Scotchlight™ reflective material products, use a technology to provide retroreflection which enables the human eye to perceive light in low-light conditions. In more scientific terms, retroreflection occurs when light rays are returned in the direction from which they came. An electromagnetic wave front is reflected back by a reflection surface, along a vector that is parallel to but opposite in direction from the wave source. The retroreflection surface's angle of incidence is greater than zero or equal to zero. This is unlike other conventional reflective surfaces such as a planar mirror, which does so only if the mirror is exactly perpendicular to the wave front (a zero angle of incidence). Retroreflective materials return a relatively large amount of reflected light directly to the original light source, such as a car's headlights. Since very little light is scattered when the light is returned, retroreflective materials appear brightest to an observer located near the original light source regardless of the observation angles. Therefore, retroreflective materials have been widely used for road signs and on garments but have not been used with small objects like eyewear.

The head strap 38 according to this embodiment may also include one or more retroreflective elements, such as one or more pieces of retroreflective fabric 44 attached on an outer side of the head strap 38 for example, by stitching. The head strap 38 also includes a pair of connectors which are sockets 46 in this embodiment to snuggly receive the free end of the respective arms 20 of the frame 12 of the glasses 10. The piece or pieces of the retroreflective fabric 44 may be attached to the flexible strap section (not indicated) extending between the two connectors (sockets 46).

FIG. 4 illustrates a head strap 48 according to another embodiment. The head strap 48 is separated into right and left sections 48a and 48b and each at one end has a connector such as the socket 46 to be attached to the respective arms 20 of the frame 12 of the glasses 10 of FIG. 1. A fastening tape such as Velcro (a trade-mark) which consists of opposite pieces 50 of nylon fabric, one with tiny hooks and the other with a dense pile, that interlock when pressed together, is attached for example, by stitching to the respective right and left sections 48a, 48b of the head strap 48. Therefore, the right and left sections 48a, 48b of the head strap 48 can be conveniently connected at a location with respect to each other to achieve a desired effective length of the head strap 48. Similar to the head strap 38 of FIG. 3, a retroreflective element such as a piece of retroreflective fabric 52 is also attached to the head strap 48, for example, by stitching. The retroreflective fabric 52 may be attached to the outside of at least one of the right and left sections which is placed as an outer layer of the overlapping sections when the right and left sections 48a, 48b are secured together by the opposite pieces 50 of the fastening tape attached thereto.

It should be understood that each piece of retroreflective fabric 44 or 52 has a retroreflective surface (a functioning surface) opposed to a back surface thereof and the retroreflective surface should be exposed visibly when the piece retroreflective fabric 44 or 52 is attached to the head strap 38 or 48.

FIGS. 5 through 10 illustrate a structure of reflective goggles 10a according to another embodiment. Goggles 10a generally includes a frame 12a which for example, may be made of a plastic material in a molding process, having a main front section 14a with opposed side ends 16a for supporting one or two lenses 18a. A head strap 54 which may be elastically extendable or flexible but not elastically extendable, is attached for example, to the opposed side ends 16a of the main front section 14a of the frame 12a. The frame 12a of the goggles 10a may or may not include one or more retroreflective elements attached thereto.

The head strap 54 of the goggles 10a may include a flexible strap section 56 which may be elastically extendable or may not be elastically extendable, and a pair of connectors 58 (only one shown in FIG. 5). Each of the connectors 58 includes a first portion 60 pivotally connected in a known or unknown manner to one of the side ends 16a of the main front section 14a of the frame 12 such that the first portion 60 is pivotal about an axis 62 with respect to the main front section 14a. The connector 58 also includes a second portion 64 which may be detachably and adjustably attached to one of the opposite ends of the flexible strap section 56 in a known or unknown manner such that the length of the flexible strap section 56 between the two second portions 64 (and thus between the two connectors 58) is adjustable. Each of the second portions 64 is detachably engaged with the first portion 60. For example, the second portion 64 may be inserted through a slot 66 defined in a free end (opposite to the end pivotally engaged with the frame 12a) into the first portion 60 wherein the second portion 64 is engaged by an "click-in" device 68a, 68b (See FIGS. 6 and 7).

Each of the first portions 60 of the connector 58 may have a retroreflective element attached thereto. In this embodiment, the first portion 60 has a recess 70 defined in an inner side (not numbered) of the first portion 60 and the recess 70 communicates with the slot 66. The recess 70 defines at least one profiled opening (a plurality of profiled openings 72 in a desired design according to this embodiment), which extends from the recess bottom through the first portion 60 to an outer side (not numbered) of the first portion 60. A piece of retroreflective fabric 74 which has reflective lenses bonded to a fabric backing to form a retroreflective surface, is placed within the recess 70 with the retroreflective surface against the recess bottom in order to expose the retroreflective surface of the fabric 74 through the openings 72 in the desired design.

A retaining member 76 is provided within the recess of each first portion 60 for retaining the retroreflective fabric 74 in place. The retaining members is formed, for example with a plate (not numbered) having first and second opposed sides (not numbered). The first side of the plate substantially corresponds with the contour of the recess bottom of the recess 70 to press the retroreflective fabric 74 against the recess bottom. The plate is thin and therefore the second side of the plate of the retaining member 76 may be substantially flush with a side edge 78 of the slot 66 in order to allow the second portion 64 to be inserted into the first portion 60.

Figure 9:
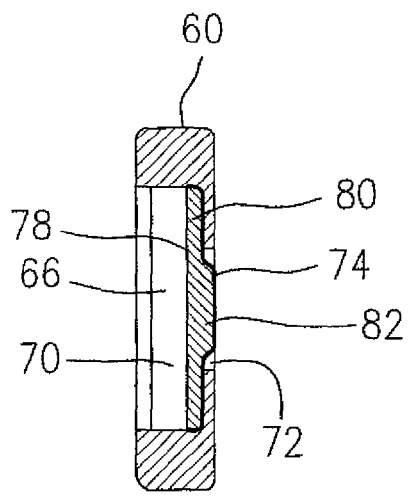
FIG. 9 is a cross-sectional view similar to FIG. 8, showing the first portion of the connector according to an alternative configuration.

In an alternative structure as shown in FIG. 9, the retaining member 80 may further include a projecting element 82 extending outwardly from the first side of the plate for pressing a portion of the piece of retroreflective fabric 74 into the opening 72 towards the outer side of the first portion 60. The number and profile of the projecting elements 82 of the retaining member 80 will correspond with the desired design of the openings 72. The retaining member 80 may be held in position by friction or adhesive.

Figure 8:
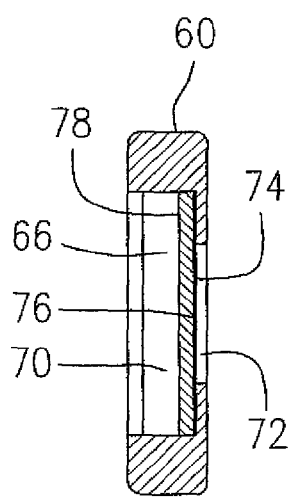
FIG. 8 is a cross-sectional view of the first portion of the connection taken along line 8-8 of FIG. 7, showing added a retaining member and a piece of retroreflective fabric received in the recess.
Figure 7:
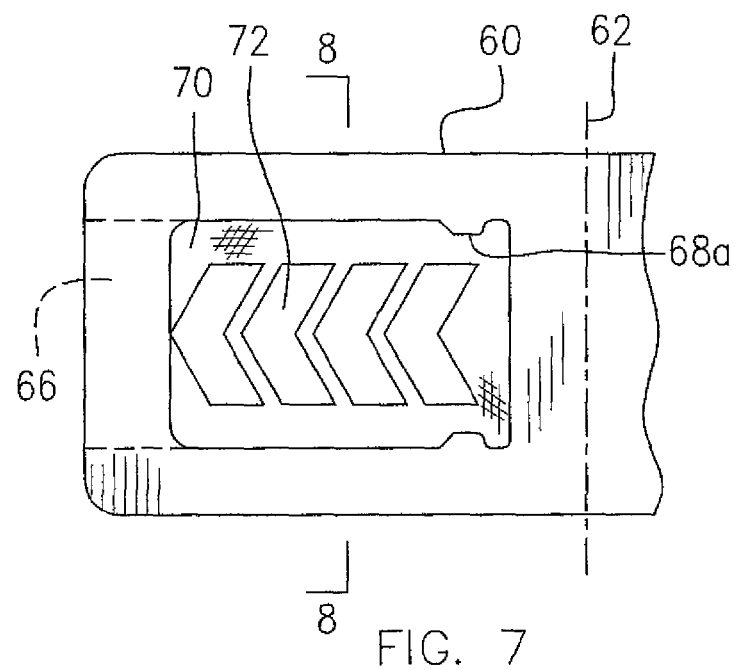
FIG. 7 is a side elevational view of an inner side of a first portion of the connector of FIG. 5, showing a recess defined therein and profiled openings (the retroreflective element being removed)
Figure 10:
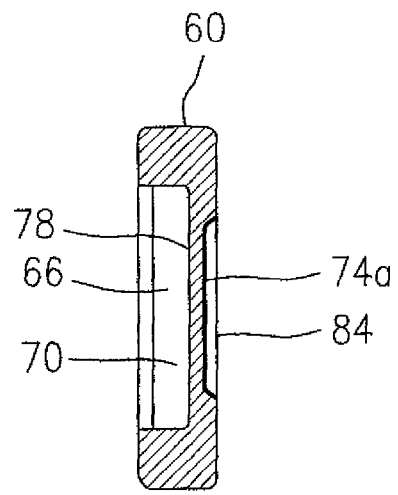
FIG. 10 is a cross-sectional view similar to FIG. 8, showing the first portion of the connector according to a further alternative configuration.

FIG. 10 illustrates a further alternative structure of the first portion 60 of the connector 58, in which components and features indicated by numerals similar to those of the first portion 60 shown in FIG. 8 will not be redundantly described herein. The difference between FIGS. 10 and 8 substantially lies in the attachment of retroreflective elements thereto. Instead of having profiled openings 72 defined in the bottom of the recess 70 of the first portion 60 as shown in FIG. 8, the first portion 60 of FIG. 10 has a profiled shallow recess 84 defined in the outer side of the first portion 60. A retrorefective element 74a such as a piece of retroreflective fabric having a shape substantially similar to the profile of the shallow recess 84, is received within the recess 84 and is attached thereto by, for example adhesive applied between the back of the retroreflective fabric and the bottom of the recess 84. The retroreflective surface of the fabric is therefore visible from the outer side of the first portion 60. The recess 70 defined in the inner side of the first portion functions only as an extension of the slot 66 for receiving the inserted second portion 64 of the connector 58.

Alternatively, the piece of retroreflective fabric used as retroreflective element 74a in the first portion 60 of FIG. 10, may be replaced by pieces of retroreflective high gloss material or retroreflective film such as pressure-sensitive adhesive film which can be conveniently attached to the recess bottom without applying additional adhesive. Transfer film may also alternatively be used as the retroreflective element 74a. Retroflective inks may also alternatively be used as the retroreflective element 74a for direct screen printing onto the recess bottom or at any location on the outer side of the connectors 58 (either first or second portions) for decorative reflective images. These and other retroreflective elements may also be used on the flexible strap section 56 of the head strap 54, particularly when the flexible strap section 56 is not elastically extendable. However, the retroreflective fabric 74 may be attached to an elastically extendable strap section by stitching the retroreflective fabric 74 on the strap section 56 when the strap section 56 is tensioned in an extended condition.

The above-mentioned alternative retroreflective materials are available in the market, and may be selected from, but not limited to 3M™ Scotchlite™ reflective materials which may be used with the head straps of glasses 10 and goggles 10a, including connectors and flexible strap sections. Any other suitable retroreflective materials may also be used as retroreflective elements for the eyewear.

The one or more retroreflective elements attached to head straps (either on connectors or flexible strap sections) of eyewear is visible by others in low-light conditions. Those retroreflective elements attached to the eyewear can be observed from wide angles relative to the safety glasses and not only from a direction restricted to a right angle relative to the reflective surface of the retroreflective elements on the glasses provided the observer is near the light source The reflective eyewear of the present invention may be configured different from what is described above and may include other components or features such as eye shields, face contact devices, etc. which are not part of this invention. The head straps applicable to this invention may be of various types and cannot be exhaustively described. Therefore, the principle of attaching retroreflective elements to head straps of eyewear may be generally applicable to other types of glasses, and is not necessarily restricted to the glasses and goggles which are described as examples to illustrate the invention, and is also generally applicable to other types of head straps and not limited to the head straps described as examples to illustrate the invention.

The embodiments of the invention described above are intended to be exemplary only. Modifications and improvements to the above-described embodiments of the present invention may become apparent to those skilled in the art in light of a review of this disclosure and are intended to fall within the scope of the appended claims.

I claim:

1. Eyewear comprising:
   at least one lens;
   a frame having a main front section for supporting the at least one lens attached to the main front section;
   a head strap attached to the frame; and
   at least one retroreflective element attached to the head strap, the retroreflective element reflecting light rays of any incidence angles along a vector parallel to but in opposite direction from a light ray source.

2. The eyewear as defined in claim 1 wherein the at least one retroreflective element is a piece of retroreflective fabric.

3. The eyewear as defined in claim 1 wherein the head strap is attached to opposed side ends of the main front section of the frame.

4. The eyewear as defined in claim 1 wherein the frame comprises a pair of arms attached to the frame pivotable with respect to the main front section, the head strap being attached to the respective arms.

5. The eyewear as defined in claim 1 wherein the head strap comprises separate right and left sections individually attached to the frame, the right and left sections being detachably connected together to form the head strap.

6. The eyewear as defined in claim 1 wherein the head strap comprises a flexible strap section and a pair of connectors, connecting opposed ends of the flexible strap section to the frame, respectively.

7. The eyewear as defined in claim 6 wherein each of the connectors comprises a first portion attached to one of the opposed side ends of and being pivotal with respect to the main front section of the frame, a second portion attached to one of the opposed ends of the flexible strap section, the first and second portions being detachably connected together.

8. The eyewear as defined in claim 7 wherein the at least one retroreflective element is attached to one of the first and second portions of each of the connectors.

9. The eyewear as defined in claim 8 wherein the at least one retroreflective element is a piece of retroreflective fabric.

10. The eyewear as defined in claim 9 wherein said one of the first and second portions of each of the connectors comprises a recess defined in an inner side thereof for receiving the piece of retroreflective fabric, the recess defining an opening extending from a recess bottom through said one of the first and second portions to an outer side of said one of the first and second portions to expose a functioning surface of the piece of retroreflective fabric.

11. The eyewear as defined in claim 10 further comprising a retaining member attached to the recess for retaining the piece of retroreflective fabric in the recess.

12. The eyewear as defined in claim 11 wherein the retaining member comprises a plate received in the recess and having first and second opposed sides, the first side substantially contoured to correspond with the recess bottom in order to allow the retroreflective fabric to be pressed by the plate against the recess bottom.

13. The structure as defined in claim 12 wherein the retaining member comprises a projecting element extending outwardly from the first side of the plate for pressing a portion of the piece of the retroreflective fabric into the opening towards the outer side of the connector.

14. The eyewear as defined in claim 6 wherein the at least one retroreflective element is a piece of retroreflective fabric stitched to the flexible strap section.

15. The eyewear as defined in claim 1 wherein the at least one retroreflective element is a piece of retroreflective high gloss material.

16. The structure as defined in claim 1 wherein the at least one retroreflective element is a piece of retroreflective pressure-sensitive adhesive film.

* * * * *